(12) United States Patent
Liu (10) Patent No.: US 7,329,852 B2
(45) Date of Patent: Feb. 12, 2008

(54) AUTOMATIC BACKGROUND REMOVAL FOR INPUT DATA HAVING CONSECUTIVE INPUT POINTS IDENTIFICATION

(75) Inventor: Canwen Liu, Belmont, MA (US)

(73) Assignee: Lambda Solutions, Waltham, MA (US)

( * ) Notice: Subject to any disclaimer, the term of this patent is extended or adjusted under 35 U.S.C. 154(b) by 1 day.

(21) Appl. No.: 11/487,777

(22) Filed: Jul. 17, 2006

(65) Prior Publication Data

US 2006/0255249 A1    Nov. 16, 2006

(51) Int. Cl.
*H01L 31/00*    (2006.01)
(52) U.S. Cl. .............................. 250/214.1; 250/214 R; 250/227.23
(58) Field of Classification Search ............. 250/214.1, 250/214 R, 221, 227.22, 227.23
See application file for complete search history.

(56) References Cited

U.S. PATENT DOCUMENTS 4,653,080 A * 3/1987 Kikuchi et al. ................. 378/7

2003/0210047 A1   11/2003 Ross et al.

FOREIGN PATENT DOCUMENTS

| EP | 0759598 A1 | 2/1997 |
| WO | WO 2006/000879 A1 | 1/2006 |

* cited by examiner

*Primary Examiner*—Que T Le
(74) *Attorney, Agent, or Firm*—Sills Cummis & Gross (57) ABSTRACT

Automatic background signal removal for input data, such as for spectrometry data, is provided. Input data includes input pixel points, such as those read by a CCD spectrometer or chromatography device, and intensity values corresponding to the data points. A distribution of changes in the intensity values between the data points is determined, and a noise level is judged by setting a threshold for the distribution. A noise region is identified as a predetermined number of consecutive input points for which the changes in the intensity values are within the noise level. Adjacent noise regions may be connected and the background signal is thus determined and subtracted. A spike noise region may also be identified and filtered, such that a peak obtained from fewer than a second predetermined number of the pixel points is determined as a spike, not a true peak. Non-spike large amplitude noises are optionally filtered.

36 Claims, 8 Drawing Sheets

A Background Removal System

FIG. 1

Algorithm Flow Chart – High Level

FIG. 2. Algorithm Flow Chart – Detail

FIG. 3

A Sample Spectrum

Manual Background Selection

Fig. 8

A Background Removal System

AUTOMATIC BACKGROUND REMOVAL FOR INPUT DATA HAVING CONSECUTIVE INPUT POINTS IDENTIFICATION

FIELD OF THE INVENTION

The present Application relates to the utilization and display of spectroscopy data, chromatography data or other input data and to the automatic removal of background signals or noise from data of a target sample.

BACKGROUND OF THE INVENTION

Spectroscopy is a widely applied analytical method for chemical and material analysis. However, background signals often inhere in spectroscopy data obtained from a target sample's spectrum, due to the sample's container, and "noises" or static produced by instrument response fluctuations, data transmission, and the like.

Removing such background signals or noise from spectral data to reveal the true signal of the sample is very important for many qualitative and quantitative spectroscopic applications. For instance, background removal is useful before entering a spectrum into a database. This is often necessary for consistency, to make all spectra have a flat background. A flat background improves overall display of the spectra, peak selection and identification, and spectral library searching. Background noise included in spectral data has a negative effect on most searching algorithms.

SUMMARY OF THE INVENTION

A background removal method, system and computer readable medium is provided. The method includes inputting input data, for example, spectral data obtained from a spectrometer or chromatography data, the input data made up of input points and intensity values corresponding to the input points. Next, a distribution of the absolute value of changes in the intensity values between the input points is determined and a noise level for the input data according to a threshold for the distribution is judged. The method further may entail identifying noise regions of the input data by identifying a predetermined number of consecutive input points for which the changes in the intensity values are within the noise level, subtracting background from the input data based on the identified noise regions; and outputting as the target sample signal the background removed data.

A noise level is judged based on the absolute values of the changes in the intensity values below the threshold, and an average, such as a median, a mode or a mean, or a range of the absolute values of the changes in the intensity values is determined for the values of the distribution above the threshold.

Optionally, the method may include identification of a spike noise region as a peak obtained from fewer than a second predetermined number of the input points.

Noise regions and line segments connecting adjacent noise regions are interpreted as the background.

Also, the input data may be first processed by normalizing and/or smoothing prior to the determining of the distribution.

When smoothed input data are processed, the background may be determined for smoothed input data and subtracted from unsmoothed input data.

Also, a spike noise region may be identified and filtered, such that a peak obtained from fewer than a second predetermined number of consecutive input points is determined as a spike.

In addition, a spike noise region can be found as a peak in which at least one of a second data point and a penultimate data point corresponds to a highest intensity point of that peak.

Further, a spike noise region may be detected as a peak region with at least two peak points within a predetermined number of consecutive data points. The predetermined number of consecutive data points may be set at five for some spectrometry applications.

DETAILED DESCRIPTION OF THE INVENTION

The following discussion describes embodiments of Applicant's invention as best understood presently by the inventor. It will be appreciated however, that numerous modifications of the invention are possible and that the invention may be embodied in other forms and practiced in other ways without departing from the spirit of the invention. Further, embodiments or features of the embodiments described may be omitted, combined selectively or as a whole with other features or embodiments, or used to replace features or embodiments, or parts thereof, without departing from the spirit of the invention. The Drawings provided herewith and the present detailed description are therefore to be considered as illustrative explanations of aspects of the invention, and should not be construed to limit the scope of the invention. The scope of the invention is defined by the below-set forth claims.

The method, system and medium described herein are based on a statistical description of the intensity distributions of spectroscopy data and signal processing. The processing includes normalization, smoothing and filtering to distinguish background data and noise signals, and thus to extract true sample spectral signals.

It will be understood that the spectral data can be from many types of biological, mineral, chemical, and materials samples. Common applications include various organic chemical samples, including but not limited to petroleum products, floral or faunal specimen, cellular products and sequences, inorganic samples, including naturally occurring or artificially produced minerals, as well as derivatives and combinations of the foregoing. Automatic background removal as described herein has application for any spectroscopy data that present sharp peaks over background, such as Raman, FT-IR, Atomic Fluorescence, NMR, MS. It is also applicable to chromatography data (which, in a broad sense, is also spectroscopy data), where a quantity (such as intensity, absorbance, abundance, response) varies as a function of time and the data presents itself in the form of peaks over background. Further, the spectral data used need not necessarily include a full spectrum obtained, or obtainable, from a sample. The present invention also has applicability in fields other than spectrometry, such as digital imaging.

Figure 3:
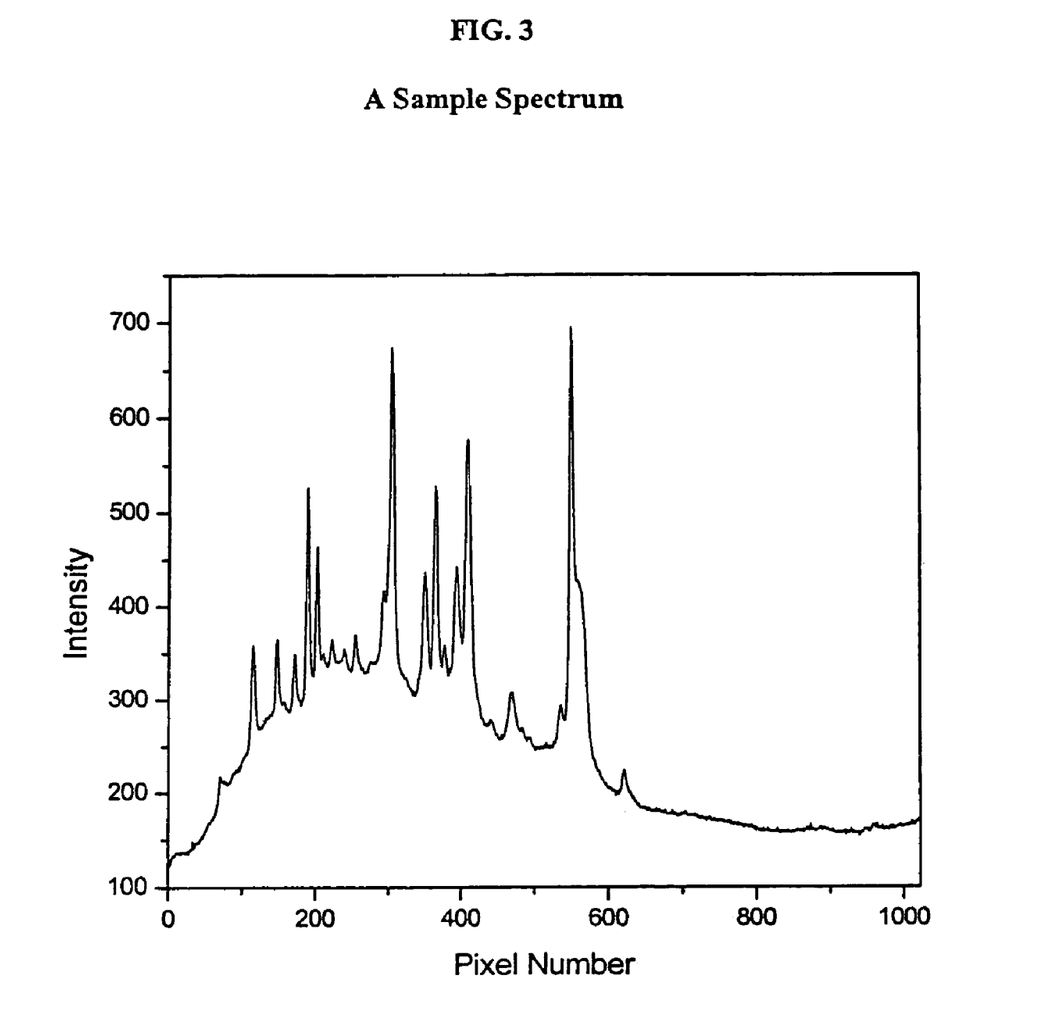
FIG. 3 shows a sample spectrum with intensities of data points plotted corresponding to the y-axis.

A spectrum consists of a series of (x, y) data point values. For example, FIG. 3 shows sample spectral data. Usually, the x point values are evenly spaced, like those corresponding to the pixel values of a CCD (charge couple device) detector, which run from the first pixel to the maximum pixel number of the CCD detector. Alternatively, a detector other than a CCD may be used to gather spectral data from a sample. Also, the spectral data previously obtained may be input from a data storage. The y data point values represents the intensity for the x pixel value. It will be understood that the (x, y) values of the input data do not have to be "Intensity" or "Pixel Numbers", so long as the data take the form of peaks over background.

In spectroscopic applications using CCD detectors, one dimension of a CCD chip surface is usually binned in one or multiple strips to generate one or multiple plots of CCD readouts (intensity values) as a function of pixel number. The x values can also be non-evenly spaced, such as the wavelength (e.g., in nanometers) or the wavenumber (e.g., in cm-1) that correspond to the pixel number of the CCD detector. For convenience, evenly spaced pixel numbers are used for x values in most of the illustrations. In this case, a spectrum is a series of intensity values (of arbitrary unit) as a function of pixel numbers.

The spectrum consists of peaks on top of a raised uneven background level. The background may be generated due to a container of the sample (a plastic capsule in the case illustrated), light scattering, and possible weak fluorescence or the like.

Figure 1:
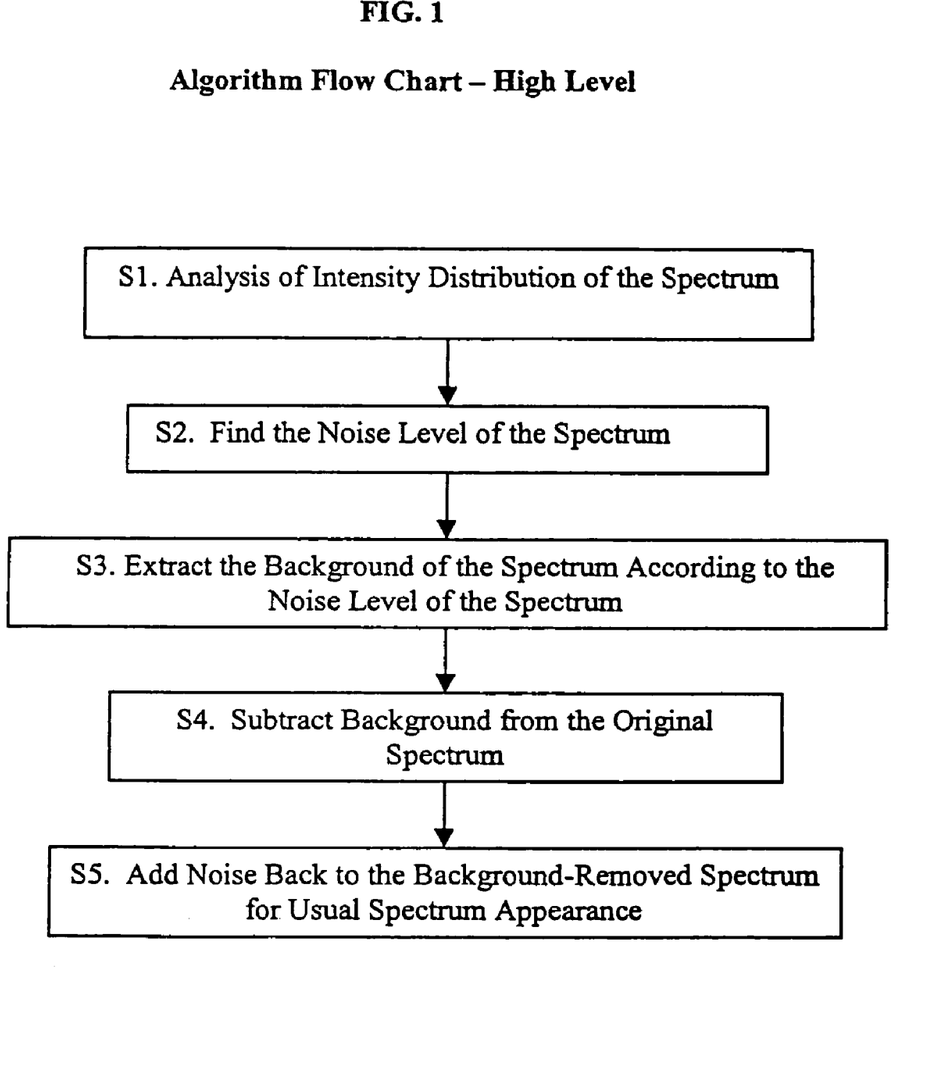
FIG. 1 is a flowchart of an automatic background removal method according to an embodiment of the present invention.

FIG. 1 is a block diagram of the automatic background removal method. What follows is a detailed illustrative example of an embodiment of the present invention, broken out into a number of major operations or steps, with reference to FIGS. 1, 3 and 4. It will be understood that these operations need not necessarily all be performed, nor need they be all necessarily performed in the following order. An example of spectrum data obtained, with the intensities shown by the y-axis is shown in FIG. 3.

At S1 of FIG. 1, the absolute value of the changes in intensity values between neighboring input points (i.e., absolute values of the first derivatives of the spectrum, AVFD) are calculated:

$$|y_{i+1}-y_{i-1}|$$

where i=0, 1, 2, . . . , N−1,

N being the maximum number of data points.

Figure 4:
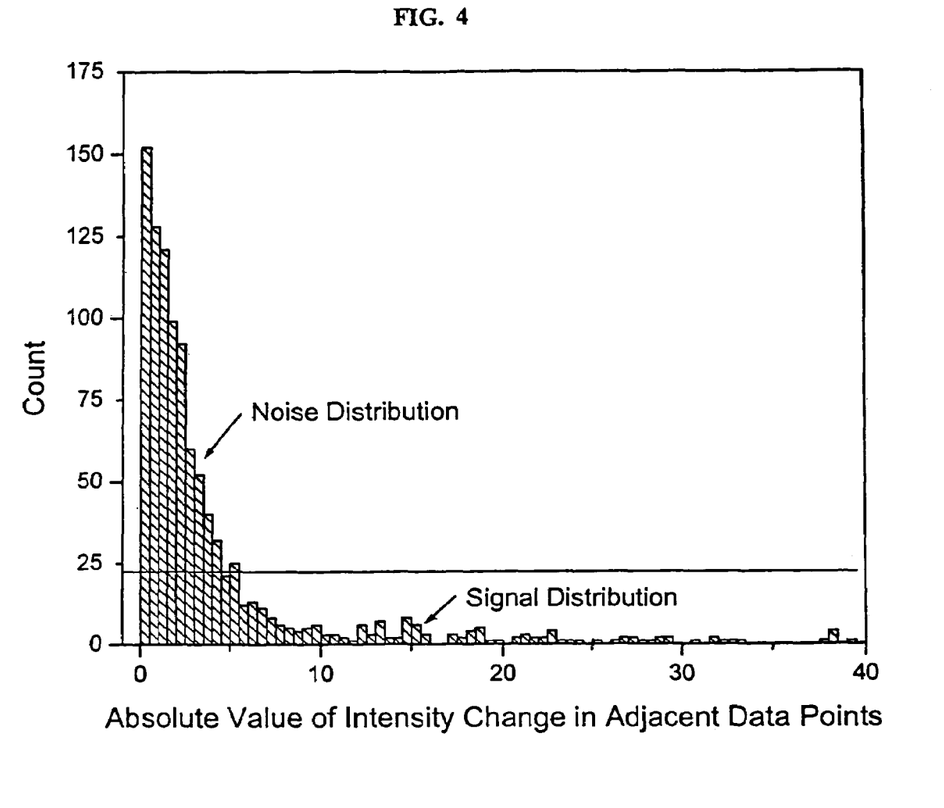
FIG. 4 shows a distribution of the absolute intensity change of the sample spectrum, according to an embodiment of the present invention.

From these N−1 AVFD values, at S2, a frequency distribution of the magnitudes of the AVFD of the spectrum is prepared. FIG. 4 shows such a frequency distribution for the exemplary spectrum of FIG. 3.

The distribution of absolute values of the intensity changes of the spectrum is analyzed. A cutoff value or threshold is empirically set to cut the tail region of the distribution corresponding to the target range. Alternatively, predetermined threshold values may be used for various types of known spectra. For example, for the distribution of FIG. 4, a cutoff value of approximately 15% of the maximum count may be used. AVFD values below this cutoff value are treated as signal distribution. The median of the remaining distribution (noise distribution) is taken as the noise level (nsLvl).

At this point, a range of intensity level changes of the target sample spectrum is established from the remaining distribution and an average, such as an arithmetic mean, median or mode may be set. The background noise level of the spectrum is thus set as being the changes in intensity values falling within the range.

At S3, the entire spectrum is analyzed according to the determined noise level of the spectrum. Noise regions may be determined as follow: any region consisting of a predetermined number of pixels whose absolute value changes in the intensity are all within the noise level. Such a predetermined number may be 5 consecutive pixels, for example, for some spectrometry applications. The whole spectrum may be searched for such noise regions.

Adjacent noise regions may then be connected by straight line segments. The noise regions and the line segments constitute the background of the spectrum.

At S4 in FIG. 1, the background of the spectrum is subtracted from the original spectrum to obtain the background-removed spectrum. The background removed spectrum constitutes peak regions and zero intensity regions, and corresponds to the true spectrum of the target sample.

Figure 5:
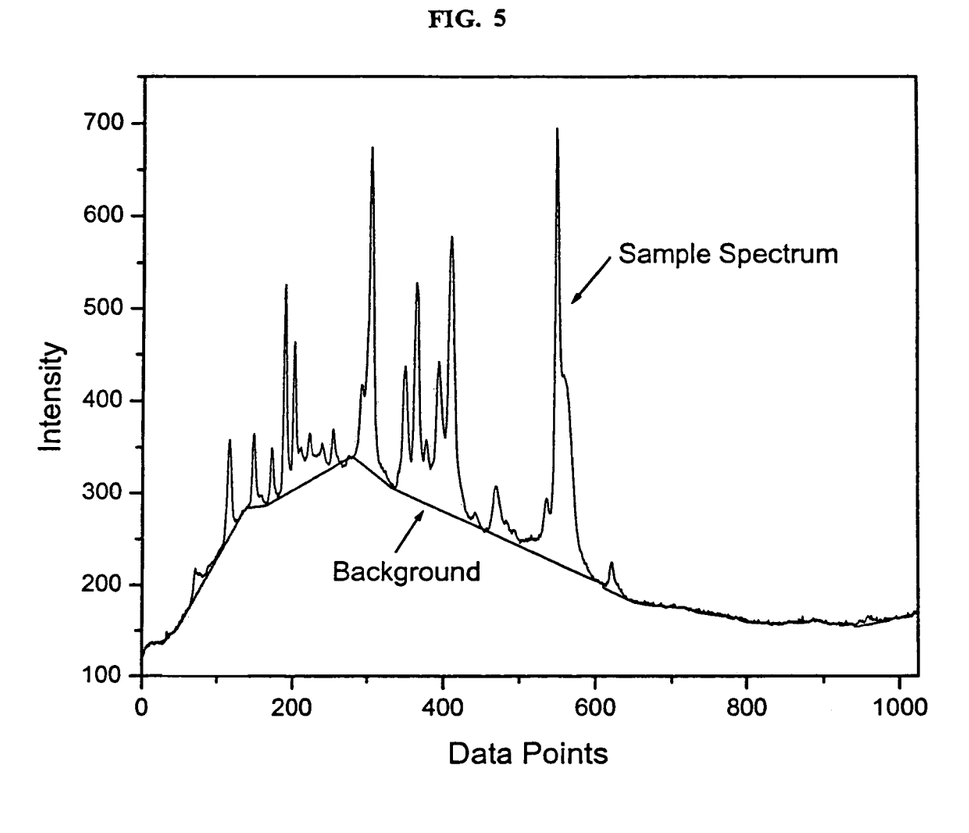
FIG. 5 shows the sample spectrum and the background removed spectrum obtained according to the present invention.
Figure 6:
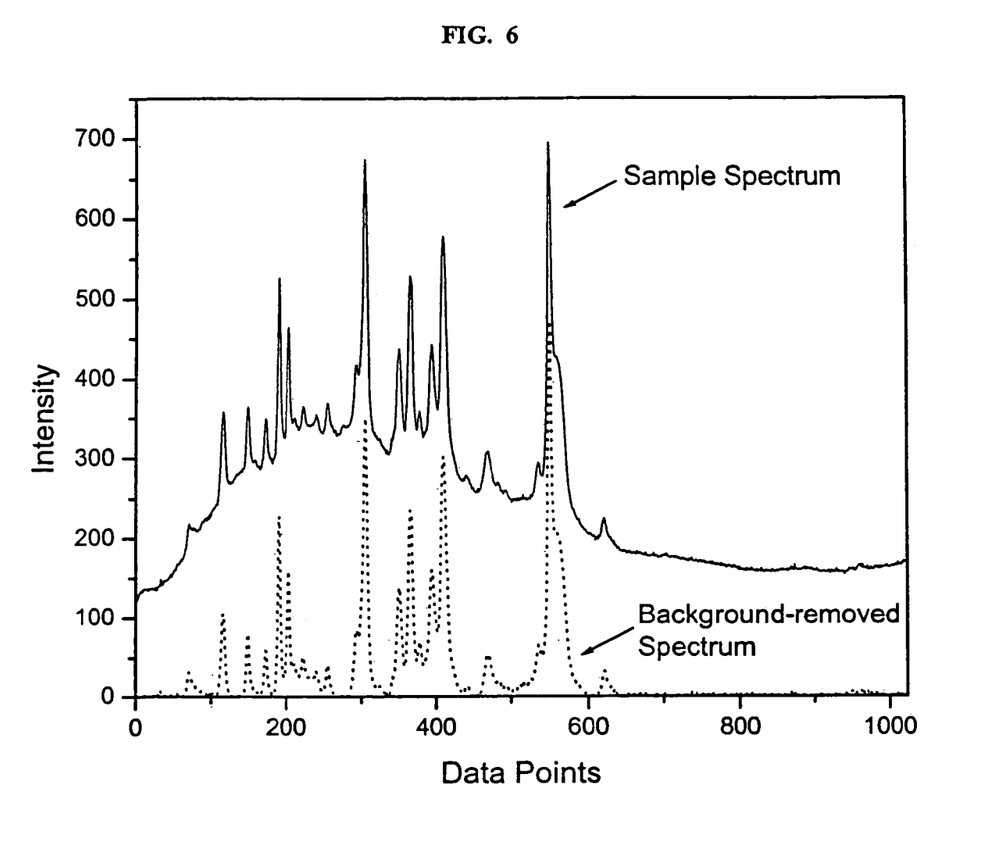
FIG. 6 shows the sample spectrum and a background removed spectrum obtained according to the present invention.

At S5, to achieve a more usual spectrum appearance in displaying the background-removed spectrum, noises within the noise level as determined above are optionally added back to the zero intensity regions of the background-removed spectrum, as shown in FIG. 5. Also, as shown in FIG. 6, such a background-removed spectrum is simultaneously displayed with the original spectrum.

Figure 2:
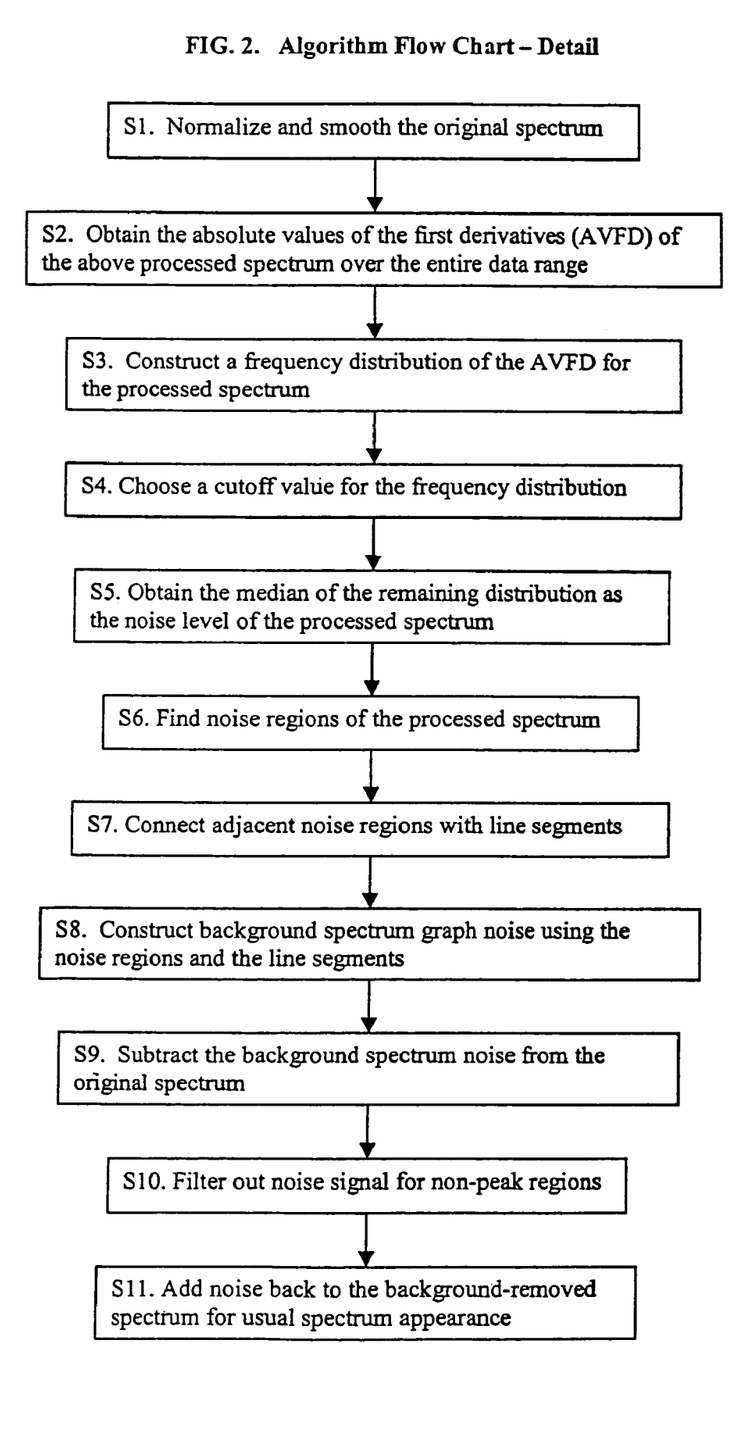
FIG. 2 is a flowchart of an automatic background removal method according to an embodiment of the present invention, with some additional details and optional features.

FIG. 2 shows the operations of FIG. 1 in more detail, as well as some optional additional operations.

According to a preferred embodiment of the present invention, before the operations above-discussed in connection with FIG. 1, the spectrum can be normalized to facilitate some parameters used to constrain the background. In this way, two consecutive line segments separated by a noise region do not form an angle that is too sharp (acute), such as an angle less than 90 degrees. This is to ensure a relatively smooth background over an entire spectrum. This is necessary when this procedure is applied to a variety of spectra with different signal intensities.

According to a preferred embodiment of the present invention, when a line segment that connects two adjacent noise regions, N1 and N2, crosses a peak region, such that the intensity values of one or more peak region points is lower than that of the corresponding line segment point(s), then the peak region point which has the maximum negative difference with the corresponding data point on the line segment is set as a background point (BP), and two line segments are then formed, such that a first line segment connects noise region N1 to the background point BP, and the second line segment connects the noise region N2 to the background point BP.

This normalization procedure may be performed in a variety of ways. According to an embodiment of the present invention, for example, normalization is accomplished by finding the maximum peak intensity of the original spectrum, and dividing the intensity value of each data point in the spectrum by that maximum peak intensity. Accordingly, every normalized spectrum has a maximum intensity of 1.0. The normalized spectrum can then be scaled up by a constant factor, such as 1000, to facilitate numerical manipulation.

Further, according to an embodiment of the present invention, an optional smoothing step is carried out to minimize the number of noisy peaks to be removed, and thus to maximize recognition of true peaks. The smoothing procedure may entail replacing the intensity values of each data point in the original spectrum by an intensity value that is the average intensity of n number of adjacent data points including the data point itself. That is, adjacent average smoothing, or moving window averaging, may be used. For example, n can be 3, 5 et cetera. Other smoothing methods can also be applied, such as Savitzsky-Golay smoothing, Fast Fourier Transforms, or the like. This normalized and/or smoothed spectrum is sometimes referred to as the processed spectrum.

According to a preferred embodiment, when smoothing is thus first used for the spectrum, the above-discussed background removal procedure is used to find the background for the smoothed spectrum, but once the background for the smoothed spectrum is identified, the background of the smoothed spectrum is then subtracted from the original sample spectrum (instead of from the smoothed or processed spectrum).

As shown in more detail in FIG. 2, according to an aspect of the present invention, after the absolute values of the intensity changes between neighboring data points are calculated (S2 of FIG. 2) and at S3 of FIG. 2 a frequency distribution (shown in FIG. 4) is generated for the spectrum shown in FIG. 3, a cutoff value or threshold is chosen at S4 of FIG. 2 to separate large intensity changes due to peak signals of the sample's spectrum from small intensity changes due to background signals.

This cutoff value may be empirically established. For the sample shown, this cutoff value may be advantageously set at around 15% of the maximum count (e.g., this cutoff value is approximately 23 for FIG. 4). At S5 of FIG. 2, the median of the remaining distribution (noise distribution) is taken as the median of the noise spectral range of the sample spectrum (e.g., 2.75). It will be understood that instead of the median of the noise spectrum range, other statistics, such as the average or mode or range may be used. This median or average or range or the like may then be used to determine peaks as follows: intensities values with changed between neighboring data points higher than the median (or other statistic) are interpreted as part of peaks.

At S6 of FIG. 2, noise level according to the noise spectrum's range is next extracted. Noise regions may be determined as follow: any region consisting of a predetermined number (m) of pixel points whose absolute value in changes in the intensity are all within the noise level are regarded as noise regions. Such a predetermined number may be 5 consecutive pixels points, for example for some spectrometry applications. The whole spectrum is searched for such noise regions, and regions that do not satisfy this criterion are regarded as part of spectral peak regions. For example, for any region that starts with data point, where $i=0, 1, 2, \ldots, N-m$ N is the maximum number of data points (e.g., maximum number of pixel points), m is the preset consecutive number of data points to satisfy the criteria, we need to have (nsLvl is the noise level):

$|y_{i+1}-y_i|<nsLvl$ $|y_{i+2}-y_{i+1}|<nsLvl$ $\ldots$ $|y_{i+m}-y_{i+m-1}|<nsLvl$ Adjacent noise regions may be connected with straight lines. A sequential connection of the noise regions and the line segments thus constitutes the background of the spectrum (lower line) shown in FIG. 5, for the sample spectrum shown in FIG. 3.

The background of the spectrum is next subtracted. To arrive at the background-removed spectrum, the background of the sample spectrum is subtracted at corresponding pixel numbers from the original sample spectrum. The background-removed spectrum consists of peak regions and zero intensity regions. Zero intensity regions occur when the background intensity values are the same as the sample spectrum intensity values.

According to a preferred embodiment, spikes may be filtered, as follows. In many spectroscopic applications, it takes a minimum of 5 data points to form a peak: 2 pixels at the base of the peak, 1 at the peak maximum, and 2 in between. Therefore, a peak with fewer than 5 data points can be regarded as a noise spike.

Also, the filtering of noises with large amplitudes may optionally be performed. Such large amplitude noises are initially taken as peak signals. According to a preferred embodiment, any peak region with more than 1 peak within 5 consecutive data points is regarded as a noise signal. The number 5 can be different in different applications according to the preferred way of defining the minimum number of data points that are need to form a peak. Other ways of filtering such as by FFT filter to filtering out the noise signals can also be employed.

According to a further embodiment of the present invention, an optional spike filtering operation is performed, such that a peak in which the second or second to the last pixel point corresponds to the highest intensity point of that peak is regarded as a spike and is filtered from the spectral data.

To achieve a more usual appearance for the report or graph that is output to a user, noise may be added back to the background-removed spectrum. In particular, the noise level of the spectrum may be added back to the zero intensity regions of the background-subtracted spectrum to give a spectrum appearance that the user is more likely to expect or recognize easily. Note that no additional noise is added to the peak regions of the spectrum. FIG. 6 shows the final background-removed spectrum (dotted curve) plotted on the same graph as the original spectrum (solid curve).

Figure 8:
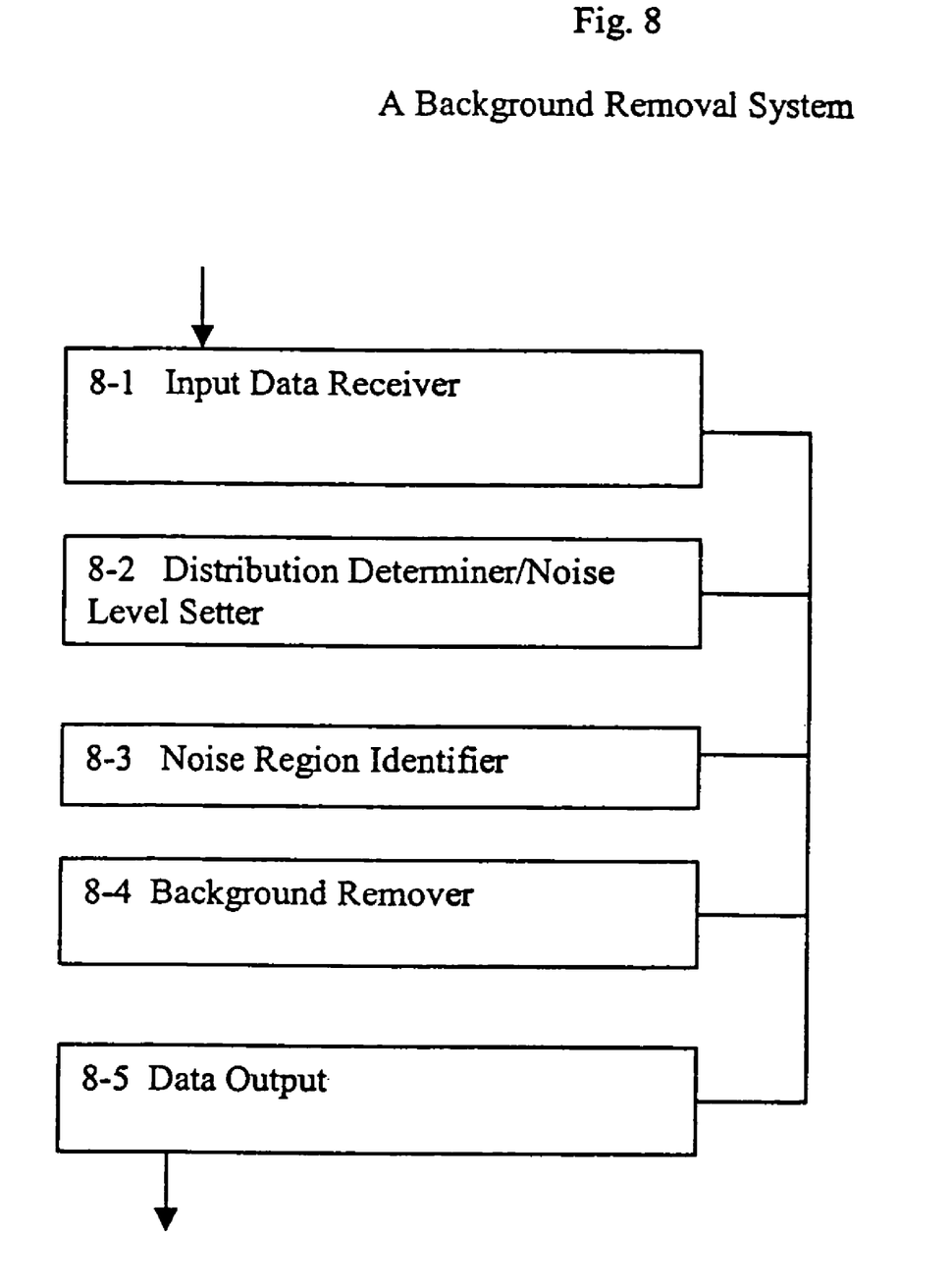
FIG. 8 shows a schematic view of an embodiment of a system according to the present invention.

Shown in FIG. 8 is a background removal system embodying a system according to the present invention. Shown as module 8-1 is an input data receiver that is designed to receive input data including the input points, such as the pixel points of a CCD spectrometer and the intensity values corresponding to the input points. The arrows show the input to and output from the system.

A distribution is determined by a noise level setter (8-2). The distribution of the absolute values of the changes in the intensity values between adjacent input points is thus determined. Also, module 8-2 judges a noise level for the input data according to a threshold for the distribution, the threshold is also set by the module 8-2.

A noise region identifier 8-3 identifies noise regions by identifying a predetermined number of consecutive input points for which the changes in the intensities are within the noise level. Adjacent noise regions thus identified may be connected by a line, also in the module 8-3.

Module 8-4 is a background remover that subtracts background signal from the spectrum of the input data based on the identified noise regions. The target sample signal is then the background removed data as output by data output 8-5.

The automatic background removal procedure stated in this invention is in most cases comparable in quality to that achieved by manual background removal.

Figure 7:
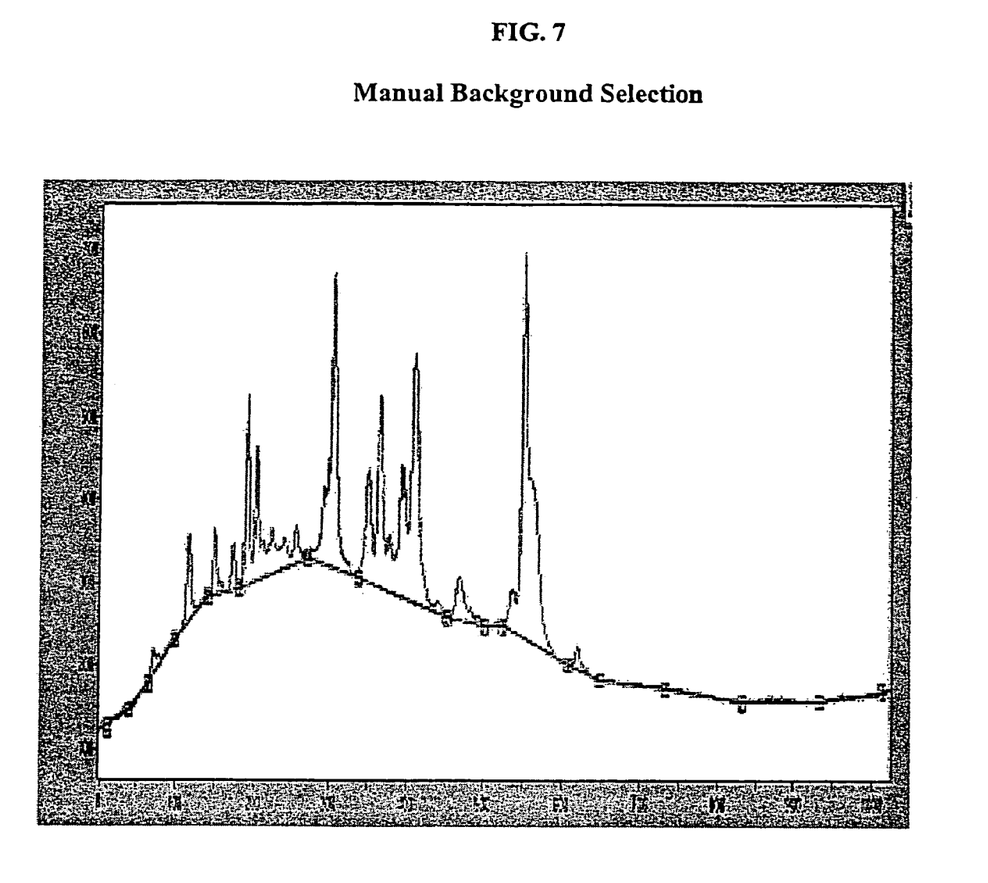
FIG. 7 shows manual background removal according to a conventional method.

Shown in FIG. 7 is a manually selected background (lower curve with square symbols) of the spectrum of FIG. 3. By clicking on user selected points on the spectrum using a competitor's analytical instrument application. Automatic background removal for spectroscopic data saves user time, and plays an especially important role in rapid material identification, including, for example, spectral library searching and automated process control utilizing spectroscopy.

It will be understood that a system according to the present invention may be implemented in a number of ways, including, but not limited to, implementations as software embodied on a recording medium readable by a data processor, as hardware, as firmware or as any combination of the foregoing, or as any other system or medium capable of carrying out the foregoing operations.

Preferred embodiments and methods of the present invention discussed in the foregoing are to be understood as descriptions for illustrative purposes only, and it will be appreciated that numerous changes, substitutions, omissions, and updates thereof are possible without departing from the spirit and scope of the claims.

What is claimed is:

1. A background removal method, comprising:
    inputting input data comprising input points and intensity values corresponding to the input points;
    determining a distribution of changes in the intensity values between the input points and judging a noise level for the input data according to a threshold for the distribution;
    identifying noise regions of the input data by identifying a predetermined number of consecutive input points for which the changes in the intensity values are within the noise level;
    subtracting background from the input data based on the identified noise regions; and
    outputting as the target sample signal the background removed data.

2. The method of claim 1, wherein the input data are one of spectral data obtained from a spectrometer and chromatography data.

3. The method of claim 1, wherein an absolute value of the change in the intensity value is determined as the change in the intensity value and wherein the noise level is judged based on the absolute values of the changes in the intensity values below the threshold.

4. The method of claim 3, wherein one of an average, a median, a mode, a mean, and a range of the absolute values of the changes in the intensity values is determined for the values of the distribution above the threshold.

5. The method of claim 1, wherein a spike noise region is identified as a peak obtained from fewer than a second predetermined number of the input points.

6. The method of claim 1, wherein the noise regions and line segments connecting adjacent noise regions are interpreted as the background.

7. The method of claim 1, wherein the input data are processed by at least one of normalizing and smoothing prior to the determining of the distribution.

8. The method of claim 7, wherein the background is determined for smoothed input data and subtracted from unsmoothed input data.

9. The method of claim 1, wherein a spike noise region is identified and filtered, such that a peak obtained from fewer than a second predetermined number of consecutive input points is determined as a spike.

10. The method of claim 1, wherein a spike noise region is identified as a peak in which at least one of a second data point and a penultimate data point corresponds to a highest intensity point of that peak.

11. The method of claim 1, wherein a spike noise region is identified as a peak region with at least two peak points within a predetermined number of consecutive data points.

12. The method of claim 11, wherein the predetermined number of consecutive data points is five.

13. A background removal system, comprising:
    an input data receiver configured to receive input data comprising input points and intensity values corresponding to the input points;
    a noise level setter configured to determine a distribution of changes in the intensity values between input points and to judge a noise level for the input data according to a threshold for the distribution;
    a noise region identifier configured to identify noise regions of the input data by identifying a predetermined number of consecutive input points for which the changes in the intensity values are within the noise level;
    a background remover configured to subtract background from the input data based on the identified noise regions; and
    a data output configured to output as the target sample signal the background removed data.

14. The system of claim 13, wherein the input data are one of spectral data obtained from a spectrometer and chromatography data.

15. The system of claim 13, wherein an absolute value of the change in the intensity value is determined as the change in the intensity value and wherein the noise level is judged based on the absolute values of the changes in the intensity below the threshold.

16. The system of claim 15, wherein one of an average, a median, a mode, a mean, and a range of the absolute values of the changes in the intensity values is determined for the values of the distribution above the threshold.

17. The system of claim 13, wherein a spike noise region is identified as a peak obtained from fewer than a second predetermined number of the input points.

18. The system of claim 13, wherein the noise regions and line segments connecting adjacent noise regions are interpreted as the background.

19. The system of claim 13, wherein the input data are processed by at least one of normalizing and smoothing prior to the determining of the distribution.

20. The system of claim 19, wherein the background is determined for smoothed input data and subtracted from unsmoothed input data.

21. The system of claim 13, wherein a spike noise region is identified and filtered, such that a peak obtained from fewer than a second predetermined number of consecutive input points is determined as a spike.

22. The system of claim 13, wherein a spike noise region is identified as a peak in which at least one of a second data point and a penultimate data point corresponds to a highest intensity point of that peak, and the spike noise region is filtered.

23. The system of claim 13, wherein a spike noise region is identified as a peak region with at least two peak points within a predetermined number of consecutive data points.

24. The system of claim 23, wherein the predetermined number of consecutive data points is five.

25. A processor readable medium embodying a background removal program of instructions comprising:
   input data receiver means for receiving input data comprising input points and intensity values corresponding to the input points;
   noise level setter means for determining a distribution of changes in the intensity values between input points and for judging a noise level for the input data according to a threshold for the distribution;
   noise region identifier means for identifying noise regions of the input data by identifying a predetermined number of consecutive input points for which the changes in the intensity values are within the noise level;
   background removal means for subtracting background from the input data based on the identified noise regions; and
   data output means for outputting as the target sample signal the background removed data.

26. The medium of claim 25, wherein the input data are one of spectral data obtained from a spectrometer and chromatography data.

27. The medium of claim 25, wherein an absolute value of the change in the intensity value is determined as the change in the intensity value and wherein the noise level is judged based on the absolute values of the changes in the intensity values below the threshold.

28. The medium of claim 25, wherein one of an average, a median, a mode, a mean, and a range of the absolute values of the changes in the intensity values is determined for the values of the distribution above the threshold.

29. The medium of claim 25, wherein a spike noise region is identified as a peak obtained from fewer than a second predetermined number of the input points.

30. The medium of claim 25, wherein the noise regions and line segments connecting adjacent noise regions are interpreted as the background.

31. The medium of claim 25, wherein the input data are processed by at least one of normalizing and smoothing prior to the determining of the distribution.

32. The medium of claim 31, wherein the background is determined for smoothed input data and subtracted from unsmoothed input data.

33. The medium of claim 25, wherein a spike noise region is identified and filtered, such that a peak obtained from fewer than a second predetermined number of consecutive input points is determined as a spike.

34. The medium of claim 25, wherein a spike noise region is identified as a peak in which at least one of a second data point and a penultimate data point corresponds to a highest intensity point of that peak.

35. The medium of claim 25, wherein a spike noise region is identified as a peak region with at least two peak points within a predetermined number of consecutive data points.

36. The medium of claim 35, wherein the predetermined number of consecutive data points is five.

* * * * *